US008657861B2

(12) United States Patent
Nakamura (10) Patent No.: US 8,657,861 B2
(45) Date of Patent: Feb. 25, 2014

(54) GAS MIST PRESSURE BATH DEVICE (75) Inventor: Shoichi Nakamura, Higashichikuma-gun (JP)

(73) Assignees: Shoichi Nakamura, Higashichikuma-Gun, Nagano (JP); ACP Japan Co., Ltd., Tokyo (JP)

( * ) Notice: Subject to any disclaimer, the term of this patent is extended or adjusted under 35 U.S.C. 154(b) by 294 days.

(21) Appl. No.: 12/735,283

(22) PCT Filed: Jun. 26, 2009

(86) PCT No.: PCT/JP2009/061718
§ 371 (c)(1),
(2), (4) Date: Jun. 29, 2010

(87) PCT Pub. No.: WO2009/157538
PCT Pub. Date: Dec. 30, 2009

(65) Prior Publication Data
US 2010/0286750 A1    Nov. 11, 2010

(30) Foreign Application Priority Data
Jun. 27, 2008   (JP) .................................. 2008-168230

(51) Int. Cl.
*A61H 33/12*   (2006.01)
(52) U.S. Cl.
USPC ................ 607/84; 607/81; 607/82; 607/83; 4/524; 4/526; 4/527; 4/534; 427/2.3; 604/23
(58) Field of Classification Search
USPC .............. 607/84, 83, 81, 82; 4/524, 526, 527, 4/534; 427/2.3; 604/23
See application file for complete search history.

(56) References Cited

U.S. PATENT DOCUMENTS

| 4,772,259 A | * | 9/1988 | Frech et al. ...................... 604/23 |
| 5,312,385 A | * | 5/1994 | Greco ........................... 604/356 |
| 5,810,795 A | * | 9/1998 | Westwood .................... 604/305 |
| 6,083,209 A | * | 7/2000 | Marasco, Jr. .................. 604/290 |
| 6,571,794 B1 | * | 6/2003 | Hansen ..................... 128/204.18 |
| 2005/0254993 A1 | * | 11/2005 | Tanaka ........................... 422/33 |
| 2008/0319400 A1 | * | 12/2008 | Thorne et al. ................. 604/191 |

FOREIGN PATENT DOCUMENTS

| JP | H07-171189 | 7/1995 |
| JP | 2005-205163 | 8/2005 |
| JP | 2007-181720 | 7/2007 |
| JP | 2007-252871 | 10/2007 |
| JP | U 3150690 | 4/2009 |
| WO | WO 2004/002393 | 1/2004 |

OTHER PUBLICATIONS

Machine Translated of Niisato (publication No. 2007-181720).*

* cited by examiner

*Primary Examiner* — Bill Thomson
*Assistant Examiner* — Sebastian X Lukjan
(74) *Attorney, Agent, or Firm* — Manabu Kanesaka (57) ABSTRACT A gas mist pressure bath device includes a living-body cover member for covering the living-body's skin or the mucous membrane and forming a space for sealing the gas mist from the gas mist generating device inside of the living-body cover member, and a pressurizing member integrally formed with the living-body cover member pressurizing the gas mist in the living-body cover member. The pressurizing member is in a form of a ring, a hollow gas collection part, or a shielding film.

10 Claims, 10 Drawing Sheets

GAS MIST PRESSURE BATH DEVICE

RELATED APPLICATIONS

The present application is National Phase of International Application No. PCT/JP2009/061718 filed Jun. 26, 2009, and claims priority from, Japanese Application No. 2008-168230 filed Jun. 27, 2008, the disclosure of which is hereby incorporated by reference herein in its entirety.

TECHNICAL FIELD

The present invention relates a gas mist pressure bath device, in which a gas mist is prepared by pulverizing and dissolving carbon dioxide, oxygen or a mixed gas of carbon dioxide and oxygen, and a liquid, and the thus prepared gas mist is directly contacted to a skin or mucous membrane of a living-body for improving a blood circulation of the living-body.

BACKGROUND ART

It has conventionally been known that carbon dioxide (carbonic acid anhydride: $CO_2$, called as "carbon dioxide" hereafter) has both properties of being not only soluble in water (water-soluble) but also soluble in fat (fat-soluble) and if, therefore, only contacting the skin or mucous membrane of the living-body being as mixed with water and fat, carbon dioxide penetrates under a subcutaneous layer and expands blood vessels around penetrated carbon dioxide, and it works to improve a blood circulation. Owing to this action of accelerating the blood circulation, it displays various physiological effects such as dropping of blood pressure, improving of metabolism or accelerating to remove pain substance or waste product. Further, it has also anti-inflammation and anti-bacterial. Therefore, carbon dioxide has recently been given attention also from viewpoints of improving health or beauty other than the purpose of medical cares.

Carbon dioxide in the tissue of the living-body works to release oxygen carried in combination with hemoglobin in a red blood cell. Around parts at a high density of carbon dioxide, the red blood cell releases more oxygen. Thus, supply of oxygen to cells by the red blood cell is mainly controlled by carbon dioxide. In short, being without carbon dioxide, hemoglobin remains as combined with oxygen and the cell becomes unable to receive oxygen. As is seen, carbon dioxide is seen as a waste product resulted from action of oxygen, however, it plays in fact very important roles in the human living-body.

Further, in recent times, oxygen of high density has also widely been known as effective in activity of metabolism, fatigue recovery, stability of blood pressure and others.

As techniques of causing the living-body to absorb carbon dioxide at the comparatively narrow limited parts thereof, there have been disclosed as following.
(1) A device, which attaches a closing simple cover to the limited part of a human body and introduces carbon dioxide into the cover for carrying out the carbon dioxide bath (refer to, for example, Patent Document 1).
(2) A device, which inserts the limited part of the human body into the closing container (otherwise, attaching the container to the limited part of the human body) and introduces carbon dioxide into the container for carrying out the carbon dioxide bath (refer to, for example, Patent Document 2).
(3) A device, which attaches to the limited part of the human body a sealing and surrounding material composed of a container having an opening such as a bag body or a tubular body, seals an absorbing assistant material of helping skin-passing absorption of carbon dioxide in order to close the interior of the sealing and surrounding material, and introducing carbon dioxide thereinto for carrying out the carbon dioxide bath by (refer to, for example, Patent Document 3).

There have been proposed by present inventors the carbon dioxide pressure bath devices which are furnished with at least gas mist generating means, pressure means, and coating members of one or two layer structures for covering the skin or mucous membrane of the living-body and for causing carbon dioxide to contact the skin or mucous membrane at pressure more than a predetermined value.

CITATION LIST

Patent Documents

Patent Document 1: Patent Laid-Open No. 07-171189
Patent Document 2: Patent Laid-Open No. 2007-252871
Patent Document 3: Domestic Re-publication WO2004/002393

SUMMARY OF INVENTION

Problems to be Solved by the Invention

However, in the devices for the prior art carbon dioxide bath described in the above mentioned patent documents 1 to 3, such problems were involved that the capacities of the container, cover or bag enclosing carbon dioxide were large, and if being wholly filled, a large quantity of carbon dioxide was consumed. But for putting the devices to practical use, it is inevitable to leave margins, to some extent, to the container, cover or bag in order to cope with users' various body figures. Making the enclosing space of carbon dioxide compact was difficult, and as a result, suppression of consuming amount of carbon dioxide was troublesome.

On the other hand, in the carbon dioxide pressure bath devices having already been proposed by the present inventors, it is possible to largely heighten an absorption rate of carbon dioxide into the skin or mucous membrane by causing carbon dioxide to contact the skin or mucous membrane at values higher than a predetermined pressure value by a pressure means, while a device like a compressor as the pressure means is necessary. Therefore, increase of cost is invited, while the device is large scaled, so that it is unsuitable to ordinary uses as in home. Further, the coating part has the complicated structure, so that a production cost rises.

Besides, there has not been present up to now a device which can absorb by skin-passing at efficiently not only carbon dioxide but oxygen and a mixed gas of carbon dioxide and oxygen.

In view of the above mentioned problems, it is an object of the invention to provide a gas mist pressure bath device which is possible to efficiently absorb even the gas of a small amount through the skin or mucous membrane of the human living-body, and can be made compact and reduce cost.

Means for Solving the Problem

For accomplishing the object, the invention is concerned with the device for causing oxygen, carbon dioxide, or a mixed gas (called as "gas" hereafter) of oxygen and carbon dioxide at a density of not less than a predetermined value to contact the skin or mucous membrane of the living-body, this device is characterized by comprising a gas mist generating means for generating and supplying a mist (called as "gas mist" hereafter) prepared by pulverizing and dissolving the gas and liquid, and a bag shaped living-body cover member for covering the living-body's skin or mucous membrane and sealing inside thereof the gas mist from the gas mist generating means in order to cause the gas mist sealed within the living-body cover member at a pressure more than the predetermined value to contact the living-body's skin or mucous membrane. Herein, the instant gas mist pressure bath device is further provided with a pressurizing means of the living-body cover for pressurizing the gas mist within the living-body cover member.

By the way, the invention refers it as "pulverizing and dissolving" to pulverize liquid into fine liquid drops, and cause to contact the gas (carbon dioxide, oxygen, or a mixed gas of carbon dioxide and oxygen).

With respect to the gas mist pressure bath of the invention, concretely, the pressurizing means of the living-body cover member is composed of the ring member, this ring member is passed at its center hole with an end of the bag shaped living-body cover member, and while taking out the gas mist from the end of the living-body cover member, the ring member is slid to the insertion side of the living body of the living-body cover member in order to reduce the capacity within the living-body cover member, thereby to carry out pressurization. At this time, in the living-body cover member, almost parallel ribs are preferably formed in a sliding direction of the ring member.

Otherwise, the pressurizing means of the living-body cover member is composed of a hollow gas collecting portion connected to the bag shaped living-body cover member, and this gas collecting portion is pressurized to exhaust the gas mist therein to carry out pressurization. At this time, a further covering member may be furnished to cover the gas collecting portion.

Further, the pressurizing means of the living-body cover member is composed of a ring member having elasticity and the living-body cover member is pressed on the outer periphery by means of the inner periphery of the ring member to carry out pressurization.

Or, the pressurizing means of the living-body cover member is composed of a shielding film made of an elastic member which partitions a living-body insertion part and a pressurizing part, and a pump connected to the pressurizing part, and the pressurization is carried out by sending air from the pump into the pressurizing part by expanding the shielding film from the pressurizing part into the living-body insertion part.

Furthermore, the pressurizing means of the living-body cover member is composed of a hollow air sending portion connected to the bag shaped living-body cover member, and this air sending portion is formed with a gas mist supply mouth introducing the gas mist from the gas mist generating means into the air sending portion, a first check valve for preventing back-flow of the gas mist supplied from the gas mist generating means and a second check valve for preventing back-flow of the gas mist sent from the air sending portion to the living-body cover member, and the air sending portion is pressed to exhaust the gas mist therein to the insertion side part of the living body of the living-body cover member so that pressurization is carried out.

On the other hand, the living-body cover member is furnished, at its opening portion, with fastening means fabricated with one or plural combination of a rubber, string or face fastener, thereby to avoid the gas mist from running away into air atmosphere. Preferably, there is provided one or plural adhesive means having viscosity to the living-body's skin or mucous membrane on the face of the living-body cover member contacting the skin or mucous membrane.

In regard to the above mentioned liquid, suitable are water, ionic water, physiological salt solution, anti-allergic agent, anti-inflammatory agent, anti-febrile, anti-fungus agent, or anti-influenza virus. Otherwise, the above liquid is water containing one or plural medicines of menthol, vitamin E, vitamin C derivative, retinol, anesthetic, cyclodextrin, complex of photocatalyst and apatite, hyaluronic acid, coenzyme Q10, seed oil, propolith, or high density carbonate spring, ionic water, physiological salt solution, anti-allergic agent, anti-inflammatory agent, anti-febrile, anti-fungus agent, or anti-influenza virus.

Grain sizes of the gas mist supplied from the gas mist generating means to the living-body cover member are suitably not more than 10 μm.

In addition, optimum pressurization by the pressurizing means of the living-body cover member is 1.02 to 2.5 air pressure. Preferably, interval pressurization (pulse pressurization) is carried out by the pressurizing means of the living-body cover member.

The living-body cover member is suitably formed with any one or plural combination of a natural rubber, silicone rubber, polyethylene, polypropylene, polyvinylidene chloride, polystylene, polyvinylacetate, polyvinylchloride, polyamide resin, polytetrafluoroethylene, woven fabric or non-woven fabric.

It is preferable that the living-body cover member has a gas mist supply opening for introducing the gas mist supplied from the gas mist generating means into the living-body cover member, and this gas mist supply opening is provided therein with the check valve.

Desirably, the gas mist generating means has a gas mist supply pipe for supplying the gas mist into the living-body cover member, and this gas mist supply pipe has a filter for removing liquid drops attached to a pipe inside. Further, a whole or one of the gas mist supply pipe is suitably composed of a cornice shaped pipe, and this gas mist supply pipe is provided with the check valve.

Advantageous Effect of the Invention

According to the gas mist pressure bath device of the invention, it is not necessary that the gas is filled overall the cover of the living-body pressure bath, and adjustment may be made each time of matching each part of the living body to be inserted, so that highly effective gas mist pressure bath may be performed while suppressing a gas using amount to a minimum.

Being a very simple structure, anybody can easily use the present gas mist pressure bath device without necessitating a large scaled facility nor choosing places. Production costs can be reduced than hitherto.

BRIEF DESCRIPTION OF DRAWINGS

FIG. 1 A generally schematic view of the gas mist pressure bath device depending on a first embodiment of the invention;

FIG. 2 Typical views for explaining using manners of the gas mist pressure bath device depending on the first embodiment of the invention;

FIG. 3 Typical views for showing examples of ribs in the first embodiment of the invention;

FIG. 4 A generally schematic view of the gas mist pressure bath device depending on a second embodiment of the invention;

FIG. 5 A generally schematic view showing deformed view of the gas mist pressure bath device depending on the second embodiment of the invention;

FIG. 6 A generally schematic view of the gas mist pressure bath device depending on a third embodiment of the invention.

DESCRIPTION OF EMBODIMENTS

In the following description, explanations will be made to embodiments of this invention, referring to the attached drawings.

First Embodiment

Figure 1:
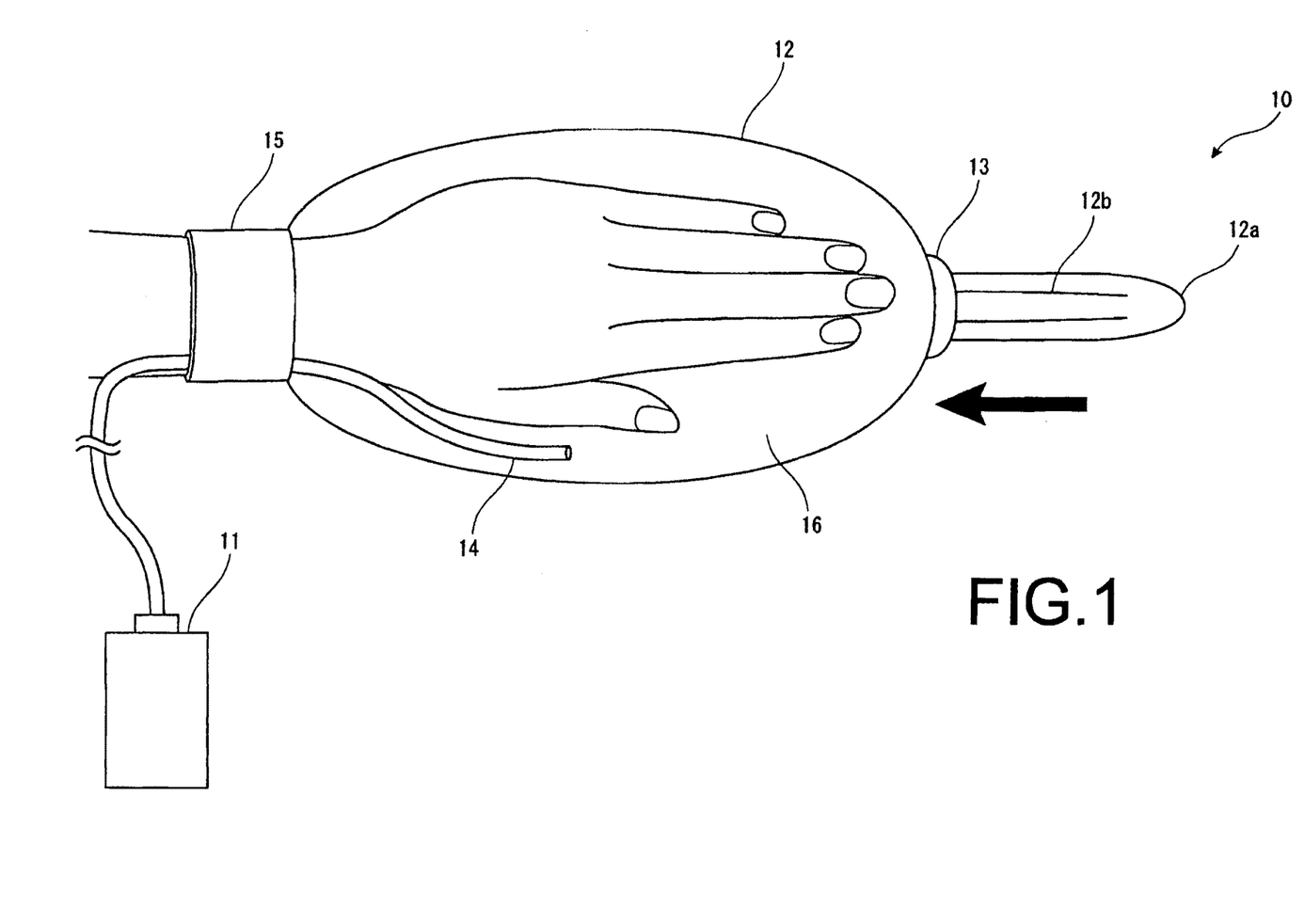
Figure 2:
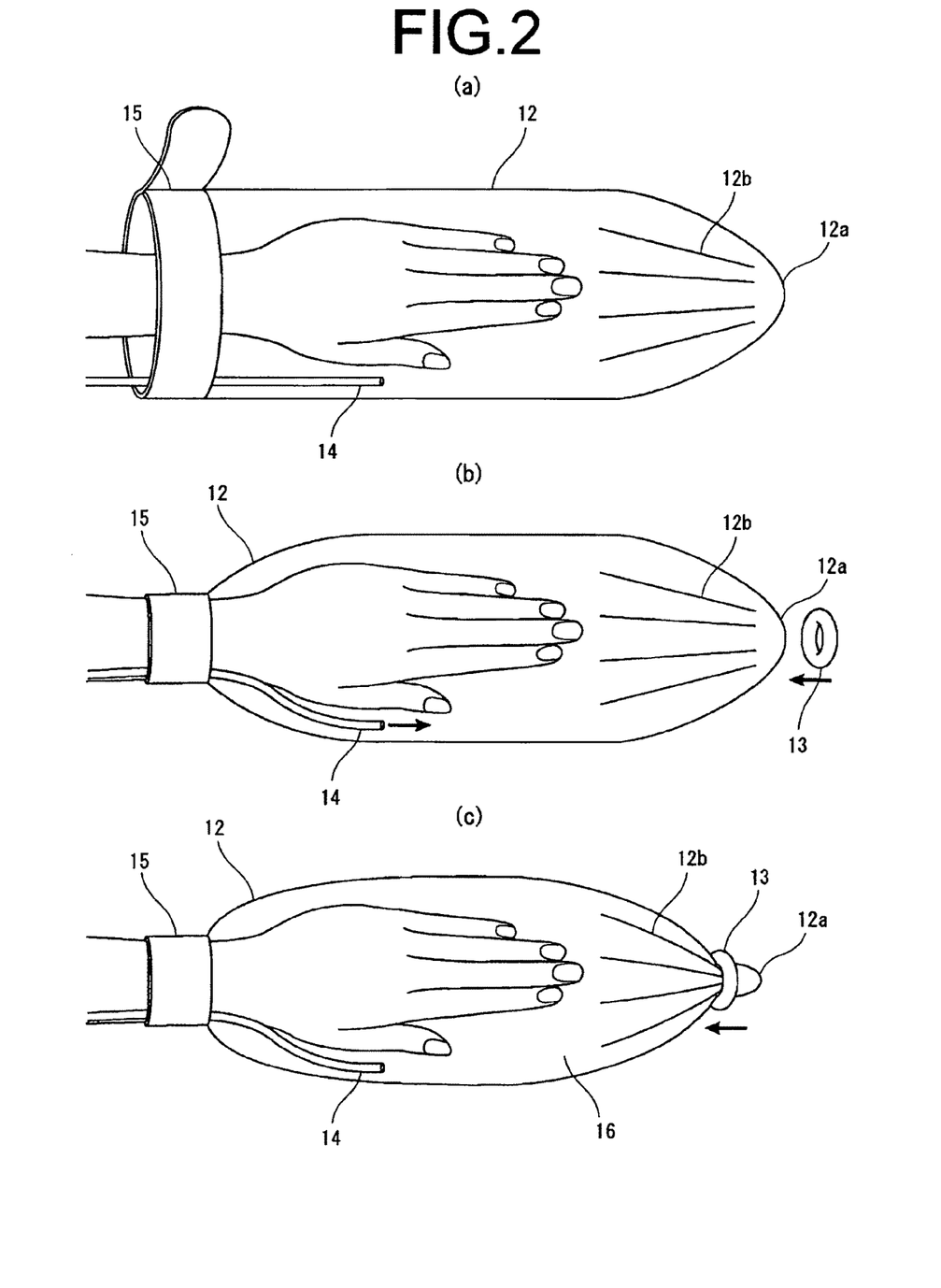

FIG. 1 is a generally schematic view of the gas mist pressure bath device depending on a first embodiment of the invention and FIG. 2 is typical views for explaining using manners of the gas mist pressure bath device.

The gas mist pressure bath device 10 of this embodiment is, as shown in FIG. 1, composed of the gas mist generating device 11 of generating and supplying the gas mist, a living-body pressure bath cover (living-body cover member) 12 for covering the limited part of the living body (herein, for example, a hand of a human living body) and causing the skin or mucous membrane of this part to directly contact and absorb the gas mist, and a reducing ring (the pressurizing means of the living-body cover member) 13.

The gas mist generating device 11 has inside a liquid supply means and a gas supply means such as a gas bomb, otherwise, this is connected to an outside liquid supply means and the gas supply means such as the gas bomb, and generates a mist (gas mist) of having pulverized and liquefied the liquid and gas, and supplies into the living-body pressure bath cover 12. For example, other than a device which is furnished with a fluid nozzle so that high flowing speed of gas from the gas supply means is utilized to pulverize and dissolve the liquid for generating the gas mist, there may be used various kinds of gas mist generating devices, for example, devices of generating the gas mist by jetting gas into the liquid at high pressure. Optimum grain sizes of the mist generated are not more than 10 μm.

In regard to the liquid to be used for generating the gas mist, other than water, ion water or physiological salt solution, it is preferable to use medical liquids useful to users' diseases, symptoms or other conditions, such as anti-allergic agent, anti-inflammatory agent, anti-analgesic and febrile agent, anti-fungus agent, or anti-influenza virus. This liquid is further possible to generate a synergistic effect with a gas physiological action by coupling with single or plurality of menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic moderating irritation to the mucous membrane; cyclodextrin removing odor; a complex of photocatalysis and apatite having disinfection and anti-phlogistic; hyaluronic acid having excellent water holding capacity and a skin moisture retention effect; coenzyme Q10 for activating cells and heightening immunization; a seed oil containing anti-oxidation and much nutrients; or propolis having anti-oxidation, anti-fungus, anti-inflammatory agent, pain-killing, anesthetic, and immunity. Further, high density carbonate spring agent having main components of carbonate and organic acid (as one example of active ingredients, sulfate, carbonate, organic acid or sodium dichloroisocyanurate) may be added.

The generated gas mist is supplied into the living-body pressure bath cover 12 through the gas mist supply pipe 14 connected to the gas mist generating device 11. Inside of the gas mist supply pipe 14, a check valve is provided for checking back flows of the gas mist. In addition, the gas mist supply pipe 14 has a liquid drop-removing filter (not shown) for removing excessive liquid drops attached to the inside of the pipe.

Figure 10:
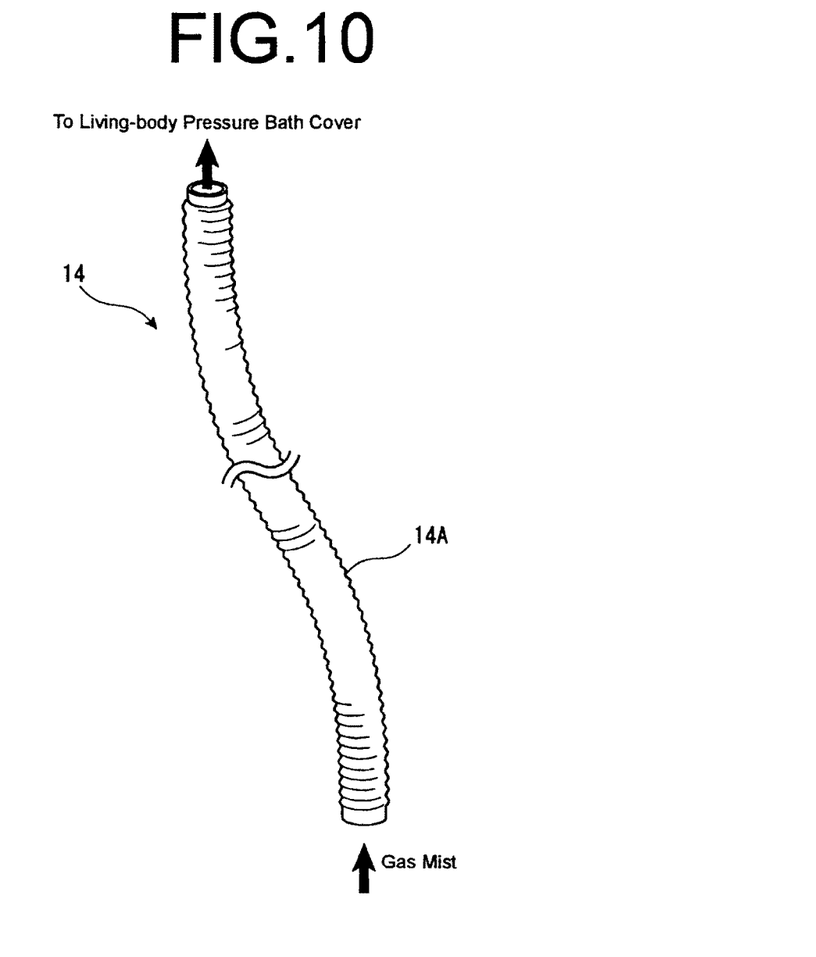
FIG. 10 A typical view showing one example of the gas mist supply pipe used to the gas mist pressure bath device depending on the invention.

Further, as shown in FIG. 10, preferably, the gas mist supply pipe 14 is overall or partially composed of a soft cornice shaped pipe 14A of a large diameter. If composing with such a cornice shaped pipe 14A, the gas mist supply pipe 14 is freely bent and may be expanded so that the user is not restricted in action. Even if the gas mist flowing in the gas mist supply pipe 14 becomes gradually liquefied, the liquid can be removed through concaves and convexes of the cornice.

The living-body pressure bath cover 12 is composed of a bag having a size as large as covering the limited part of the living-body (herein, as the example, the human living body's hand). The bag has a stopper 15 at its opening for avoiding the gas mist from leaking. The stopper 15 is preferably fabricated with, for example, an elastic face fastener, otherwise, may be coupled with single of or combination with a string, rubber or magnet. Besides, for heightening a sealing capacity within the living-body pressure bath cover 12, the stopper 15 may be arranged with a material adhering the skin or mucous membrane at an inside of the stopper 15 or living-body pressure bath cover 12, i.e., at the side contacting to the user's skin or mucous membrane. The adhesive material is preferably a viscoelastic gel of polyurethane or silicone rubber, and such a material is optimum which is exchangeable each time when viscosity becomes weak.

The living-body pressure bath cover 12 is made of the woven or non-woven fabric of a non-expansible, non-air permeable and non-moisture permeable material, for example, preferably, the natural rubber, silicone rubber, polyethylene, polypropylene, polyvinylidene, polystylene, polyvinylacetate, polyvinyl chloride, polyamide resin, polytetrafluoroethylene.

Figure 3:
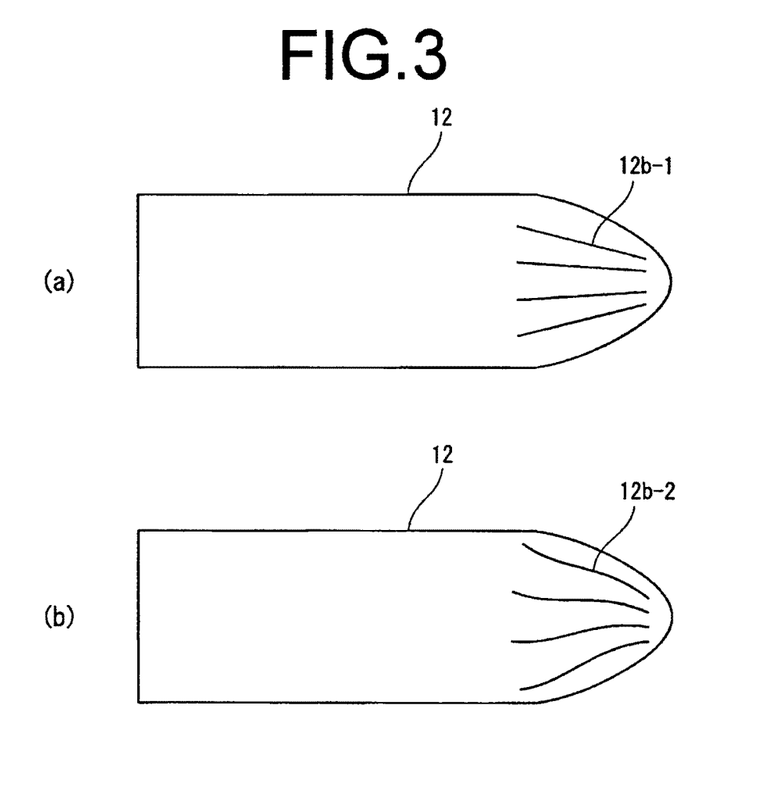

Nearly an end portion 12a of the bag forming the living-body pressure bath cover 12, for easily squeezing the end 12a and easily sliding the reducing ring 13, there are preferably formed ribs (lines) 12b almost parallel in a sliding direction of the reducing ring 13. FIG. 3 shows examples of the ribs 12b. As seen, the ribs 12b may be linear (12b-1) or curve (12b-2).

The reducing ring 13 is the pressurizing means of the living-body cover member, which passes the end 12a of the living-body pressure bath cover 12 into its central hole, slides to an insertion side of the user's limited part, and pressurizes (around 1.02 to 2.5 air pressure) the inside of the living-body pressure bath cover 12 while extracting gas mist having gathered at the end 12a to the insertion side of the user's limited part. Therefore, the reducing ring 13 is preferably made of an elastic member (for example, rubber or the like), because when attaching to the living-body pressure bath cover 12, the reducing ring 13 extends for passing the end 12a through its central hole, and after then reduces for extracting the gas mist gathering at the end 12a.

Referring to FIG. 2, explanation will be concretely made to the method of the gas mist pressure bath using the gas mist pressure bath device depending on the embodiment, referring to FIG. 2. At first, as shown FIG. 2(a), the bag shaped living-body pressure bath cover 12 is expanded, the user's limited part to be performed with the gas mist pressure bath (herein, as the example, the human body's hand) is inserted into the living-body pressure bath cover 12. Further, the gas mist supply pipe 14 connected at its one end to the gas mist generating device 11 is also inserted at its other end into the living-body pressure bath cover 12.

Next, under a condition of extracting air in the living-body pressure bath cover 12 as much as possible, the stopper 15 is fastened as shown in FIG. 2(b), and the interior of the living-body pressure bath cover 12 is made substantially shut tightly. Subsequently, the gas mist from the gas mist generating device 11 is supplied through the gas mist supply pipe 14 and forms a gas mist storage 16. At this time, it is not necessary to fill the gas mist in the whole of the living-body pressure bath cover 12. When storing the gas mist of necessary minimum within the living-body pressure bath cover 12, the gas mist supplied from the gas mist generating device 11 is stopped.

As shown in FIG. 2(c), the end 12a of the living-body pressure bath cover 12 is passed in the central hole of the reducing ring 13, the living-body pressure bath cover 12 is squeezed at the end 12a, and while extracting the gas mist at the side of the end 12a through the central hole of the reducing ring 13, the reducing ring 13 is slid toward the gas mist storage 16. Thereby, the capacity of the gas mist storage 16 becomes gradually smaller and the interior of the living-body pressure bath cover 12 is pressurized. The reducing ring 13 is slid until a moderately pressing condition, and fixedly stopped there. Holding this condition, the gas mist pressure bath is carried out to the user's limited part. Thus, by keeping the moderately pressurizing condition within the living-body pressure bath cover 12, the gas mist filled in the living-body pressure bath cover can be efficiently absorbed into the skin or mucous membrane.

By the way, the present embodiment can also employ a clip as the pressurizing means of the living-body cover member instead of the reducing ring. In short, if it is possible that the end of the living-body cover member is kept as a condition of extracting the gas mist and the moderately pressurizing condition is held at the gas mist storage, any means is available. In this embodiment, the living-body cover member pressurizing means (reducing ring) is structured to be manually slid and fixed, and an embodiment may be allowed which carries out such performance mechanically by, for example, a driving device. In addition, since pressurization in the gas mist pressure bath heightens the effects by pressurizing in pulsing at predetermined interval, the pressurizing means (reducing ring) of the living-body cover member may be slid intermittently at fixed rhythm. As to the pressurizing interval at such a case, if synchronizing with pulsations, the effects are more heightened.

Further, this embodiment has been explained, referring to the hand of the human body as the living-body's limited part about practicing the gas mist pressure bath, but may be applied to many parts as feet and other parts. In particular, according to this embodiment, since the size of the gas mist storage may be altered each time by sliding the pressurizing means (reducing ring) of the living-body cover member, if preparing in advance a large sized living-body pressure bath cover, this can be used even if human body figures change as adults and children without preparing the living-body pressure bath covers per each of different parts of living bodies.

Second Embodiment

Figure 4:
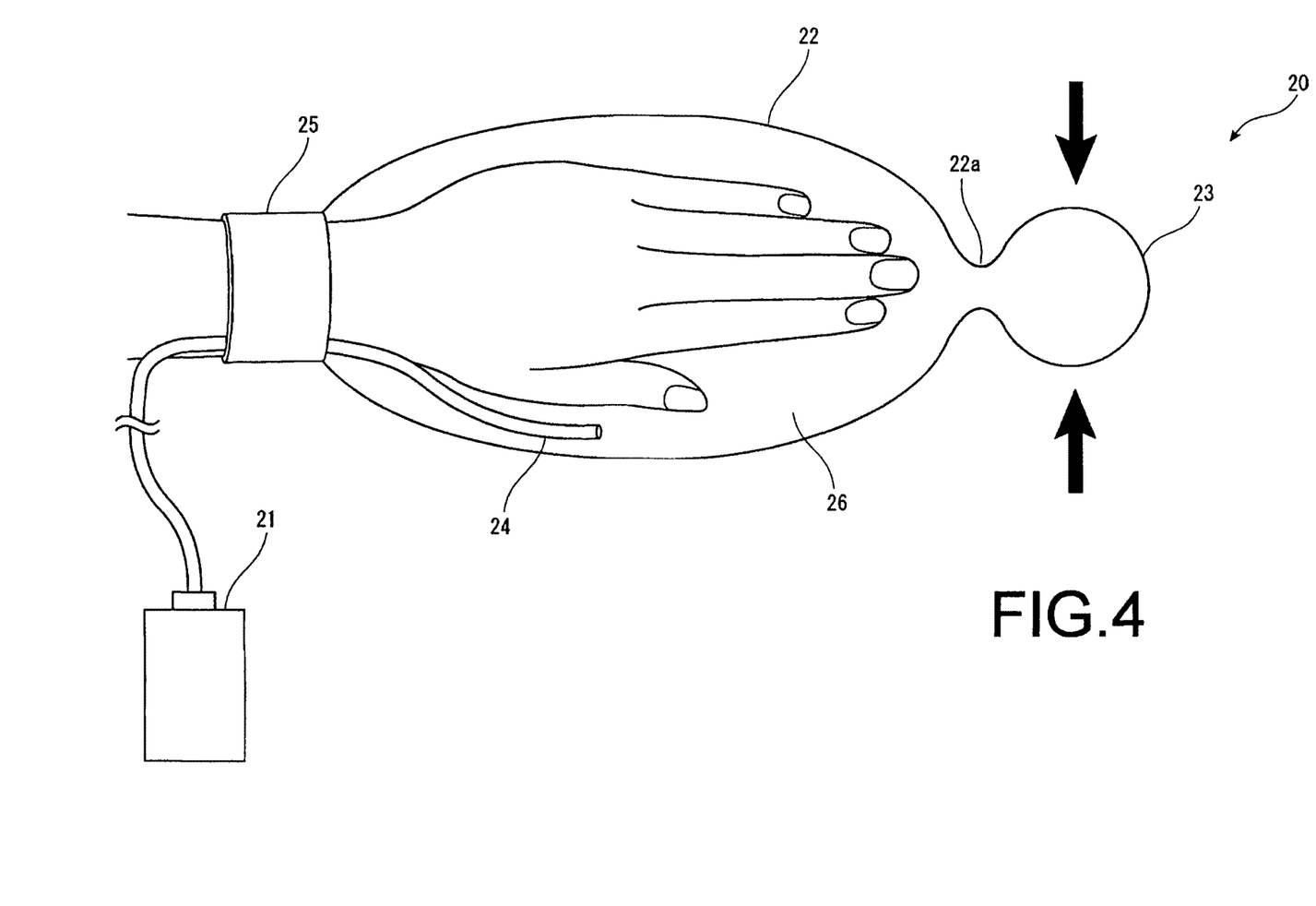

FIG. 4 is a generally schematic view of the gas mist pressure bath device depending on a second embodiment of the invention. The gas mist pressure bath device of this embodiment has the same structure of the first embodiment other than the structure in relation with the shape of the living-body pressure bath cover, and explanation thereof will be omitted in the following.

The gas mist pressure bath device 20 of the present embodiment is, as shown in FIG. 4, composed of the gas mist generating device 21 of supplying the gas mist and the living-body pressure bath cover 22 of a bag shape covering the user's limited part (herein, as the example, the human body's hand) for causing the skin or mucous membrane of this living body part to directly contact the gas mist and to absorb the gas mist. The living-body pressure bath cover 22 has a narrowed portion 22a nearly its end, and a substantially ball like pressurizing part (gas storage) 23 as a living-body cover pressurizing mean at the end side than the narrowed portion 22a.

For practicing the gas mist pressure bath, the bag shaped living-body pressure bath cover 22 is expanded, and the gas mist supply pipe 24 connected at its one end to the gas mist generating device 21 is inserted thereinto together with the user's limited part to be effected with the gas mist pressure bath. Air in the living-body pressure bath cover 22 is extracted as much as possible and the stopper 25 is attached to make substantially closed in the living-body pressure bath cover 22. Subsequently, the gas mist from the gas mist generating device 21 is supplied through the gas mist supply pipe 24, and when storing the gas mist of necessary minimum within the living-body pressure bath cover 22, the gas mist supplied from the gas mist generating device 21 is stopped. The gas mist in the pressurizing part 23 is exhausted to the side of the gas mist storage 26 by pressurizing as crushing the pressurizing part 23 of the living-body pressure bath cover 22 to make the inside of the living-body pressure bath cover 22 moderate (around 1.02 to 2.5 air pressure). Thereby, the gas mist filled in the living-body pressure bath cover 22 can be efficiently absorbed into the skin or mucous membrane of this living part.

Figure 5:
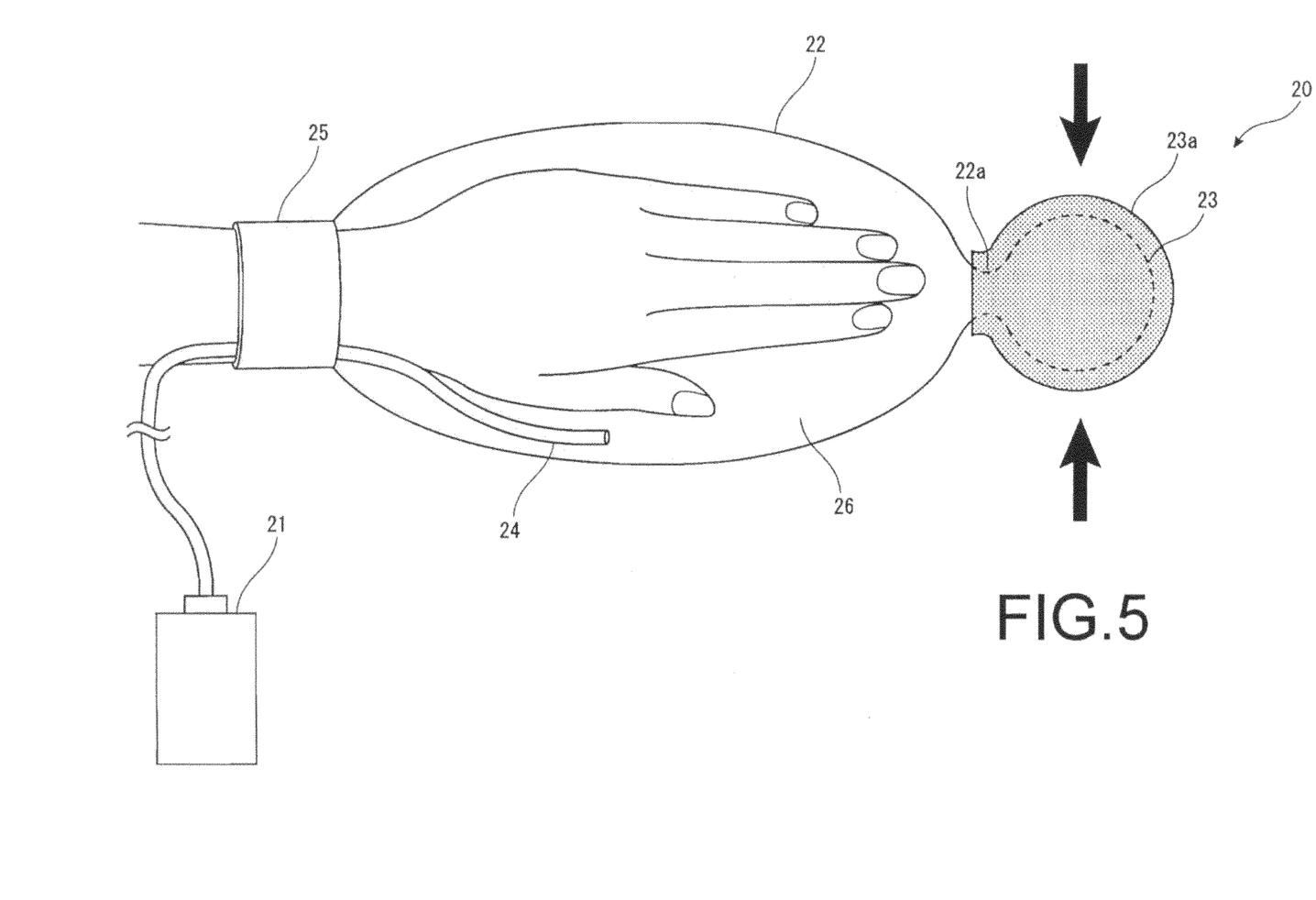

By the way, the pressurizing part 23 may be provided with an exclusively used cover. FIG. 5 is a generally schematic view showing a deformed example of the gas mist pressure bath device depending on the second embodiment of the invention. As shown in FIG. 5, the pressurizing part 23 is covered with a substantially spherical cover 23a having flexibility and elasticity. With such a structure, the pressurizing part 23 can increase its strength and using feeling. This pressurizing part cover 23a may have a structure enabling to remove the pressurizing part cover 23a only or together with the pressurizing part 23 from the living-body pressure bath cover 22.

The above mentioned embodiment has the structure pressing the pressurizing part 23 manually, but may carry out it mechanically with the driving device. Further, since pressure in the gas mist bath heightens effect by doing in pulse at predetermined interval, the pressurizing part 23 may be pressurized intermittently at constant rhythm. Pressurizing interval then heightens effects by synchronizing with stroke of pulsation.

Third Embodiment

Figure 6:
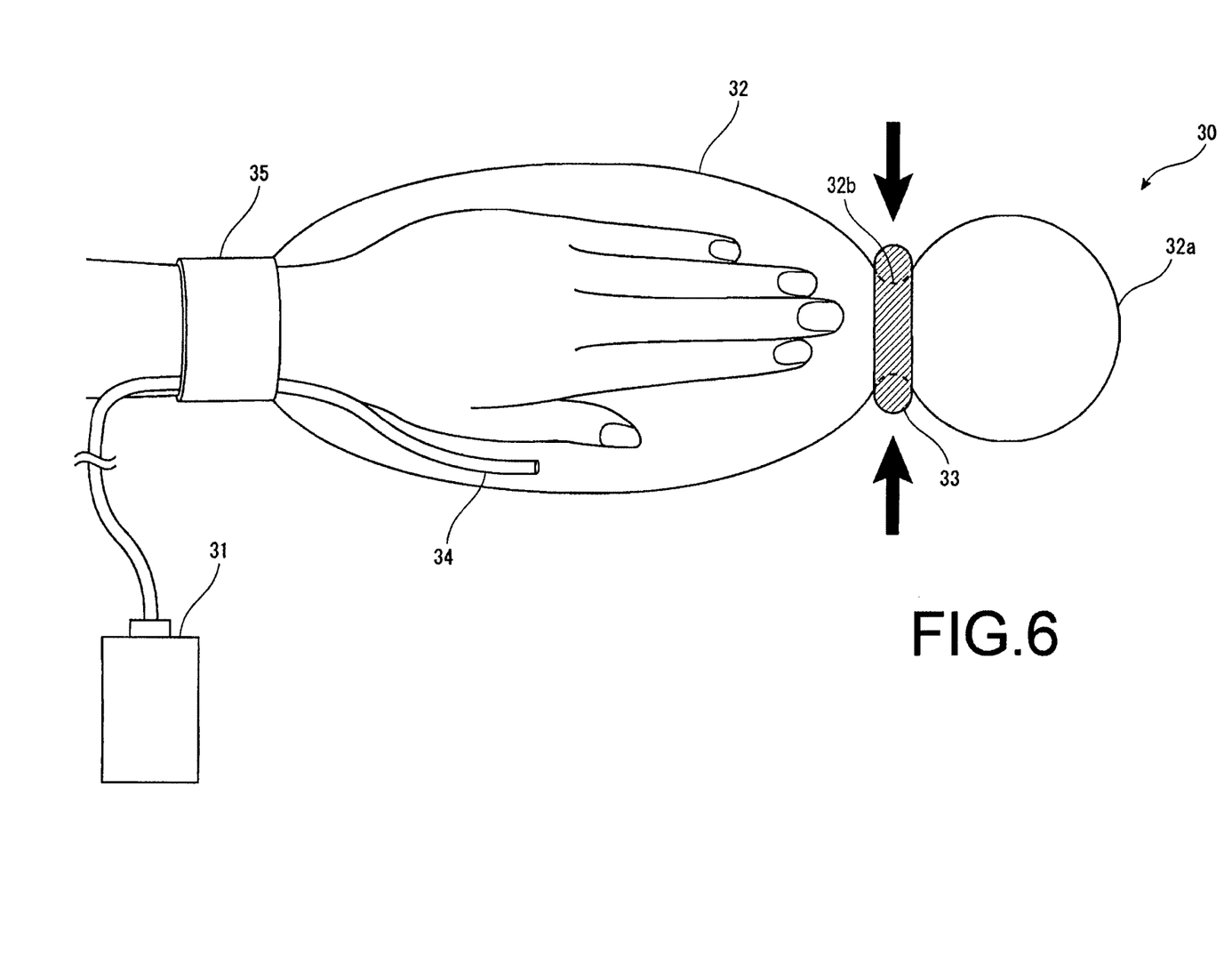

FIG. 6 is a generally schematic view of the gas mist pressure bath device depending on a third embodiment of the invention. The gas mist pressure bath device of this embodiment has the same structure of the first embodiment other than the structure in relation with the shape of the living-body pressure bath cover, and explanation thereof will be omitted in the following.

The gas mist pressure bath device 30 of the present embodiment is, as shown in FIG. 6, composed of the gas mist generating device 31 of supplying the gas mist, the living-body pressure bath cover 32 of a bag shape for covering the user's limited part (herein, as the example, the human body's hand) to cause the skin or mucous membrane of this living part to directly contact and absorb the gas mist, and a pressurizing ring 33 as the pressing means of the living-body cover member of pressurizing (around 1.02 to 2.5 air pressure) the gas mist sealed in the living-body pressure bath cover 32.

The living-body pressure bath cover 32 has a narrowed portion 32*b* for easily catching a pressurizing ring 33 in vicinity of the end 32*a*. The pressurizing ring 33 is composed of an elastic member such as a ring having inside, e.g., a coil spring or a rubber ring, and attached to the narrowed portion 32*b*, and pressurizes the living-body pressure bath cover 32 to effect moderate pressurization (around 1.02 to 2.5 air pressure).

For practicing the gas mist pressure bath, the bag shaped living-body pressure bath cover 32 is expanded, and the gas mist supply pipe 34 connected at its one end to the gas mist generating device 31 is inserted thereinto together with the user's limited part to be effected with the gas mist pressure bath. Air in the living-body pressure bath cover 32 is extracted as much as possible and the stopper 35 is attached to make substantially closed in the living-body pressure bath cover 32. Subsequently, the gas mist from the gas mist generating device 31 is supplied through the gas mist supply pipe 34, and when storing the gas mist of necessary minimum within the gas mist storage 36, the gas mist supplied from the gas mist generating device 31 is stopped. Then, the pressurizing ring 33 is positioned on the narrowed portion 32*b* of the living-body pressure bath cover 32. The inside of the living-body pressure bath cover 32 is moderately pressurized by shrinking of the pressurizing ring 33. Thereby, the gas mist filled in the living-body pressure bath cover 32 can be efficiently absorbed into the skin or mucous membrane of this living part.

Fourth Embodiment

Figure 7:
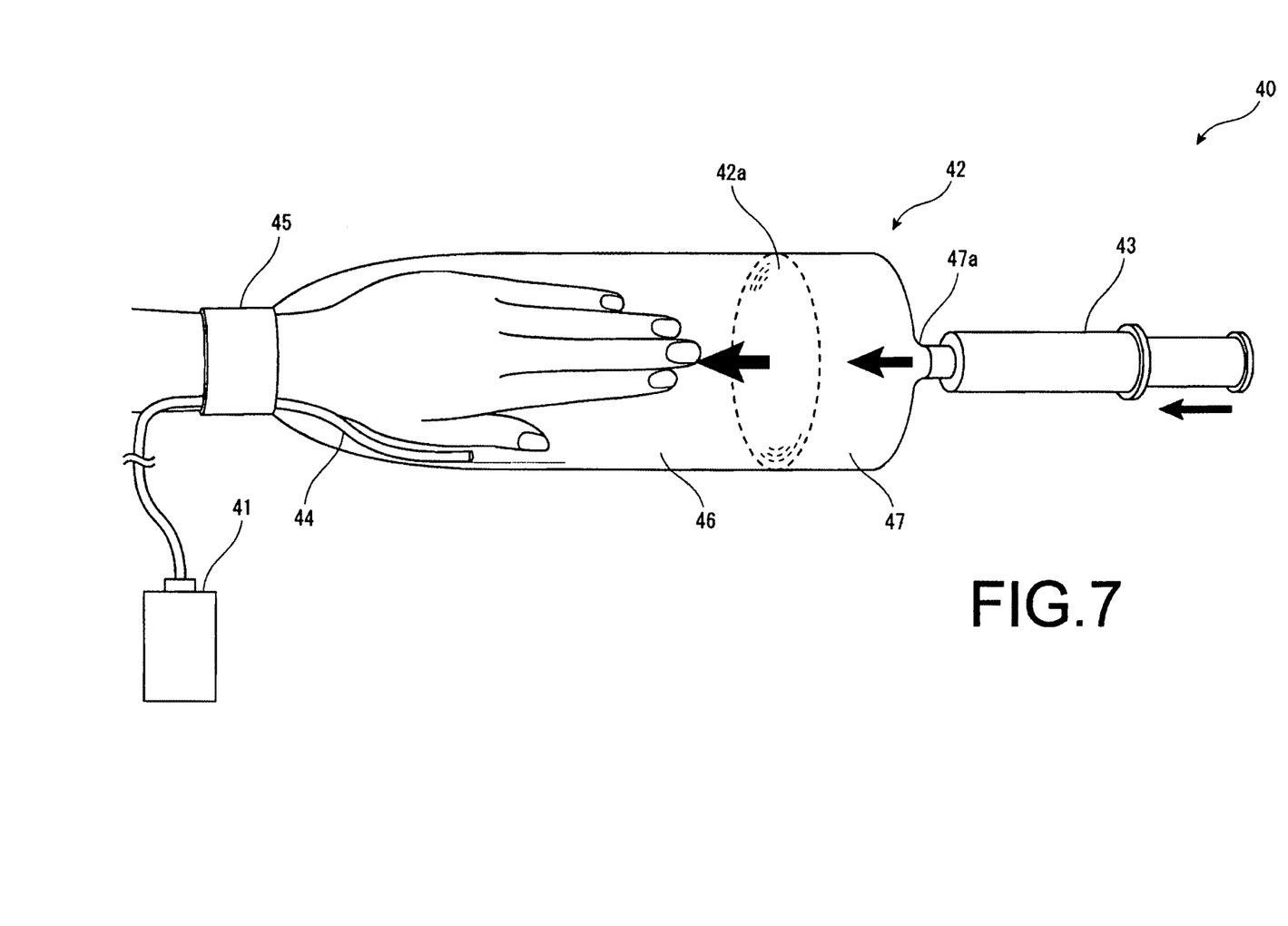
FIG. 7 A generally schematic view of the gas mist pressure bath device depending on a fourth embodiment of the invention.

FIG. 7 is a generally schematic view of the gas mist pressure bath device depending on a fourth embodiment of the invention. The gas mist pressure bath device of this embodiment has the same structure of the first embodiment other than the structure in relation with the shape of the living-body pressure bath cover, and explanation thereof will be omitted in the following.

The gas mist pressure bath device 40 of the present embodiment is, as shown in FIG. 7, composed of the gas mist generating device 41 of supplying the gas mist, the living-body pressure bath cover 42 of the bag shape covering the user's limited part (herein, as the example, the human body's hand) for causing the skin or mucous membrane of this living part to directly contact the gas mist, and a pump (syringe) 43 for pressurizing (around 1.02 to 2.5 air pressure) the gas mist sealed in the living-body pressure bath cover 42. In addition, the living-body pressure bath cover 42 is furnished inside with a shielding film 42*a* for dividing the interior of the living-body pressure bath cover 42 into the gas mist storage 46 (the side of inserting the user's limited part) and the pressurizing part 47. The above mentioned syringe 43 is connected to the pressing part 47.

The shielding film 42*a* is composed of a material having elasticity, non-permeability and non-moisture penetration. Silicon rubber or latex rubber are, for example, suitable. The gas mist storage 46 partitioned with the shielding film 42*a* is inserted into with the user's limited part, and at the same time, the pressurizing part 47 partitioned similarly with the shielding film 42*a* is fed with air within the syringe 43.

For practicing the gas mist pressure bath, the bag shaped living-body pressure bath cover 42 is expanded, and the side of the gas mist storage 46 is inserted with the limited part of the user performing the gas mist pressure bath together with the gas mist supply pipe 44 connected at its one end to the gas mist generating device 41. Under a condition of extracting air in the gas mist storage 46 as much as possible, the stopper 45 is attached to make substantially closed in the gas mist storage 46. The syringe 43 is connected at its front end to a connecting part 47*a* provided in the pressurizing part 47, enabling to feed air within the cylinder of the syringe 43. At this time, the pressurizing part 47 is filled with air in advance to a certain extent (to such an extent that the shielding film 42*a* is not expanded to the side of the gas mist storage 46).

Subsequently, the gas mist from the gas mist generating device 41 is supplied into the gas mist storage 46 through the pressurizing ring pipe 44, and when collecting the gas mist of necessary minimum, the supplying is stopped. Air in the cylinder of the syringe 43 is pushed out by a piston into the pressurizing part 47. Since the pressurizing part 47 has already been filled with air, and if further sending air from the syringe 43, an over pressurized condition is formed, and the shielding film 42*a* of the elastic material expands like a balloon toward the gas mist storage 46. When the shielding film 42*a* expands toward the gas mist storage 46, the capacity of the gas mist storage 46 is made narrow, and the gas mist storage 46 turns out a pressurized condition (around 1.02 to 2.5 air pressure). Thereby, the gas mist filled within the living-body pressure bath cover 42 is efficiently absorbed into the skin or mucous membrane.

The above embodiment is structured to manually send air from the syringe 43 to the pressurizing part 47, but the performance may be carried out mechanically by, for example, the driving device. In addition, since pressurizing in the gas mist pressure bath heightens the effects by pressurizing in pulsing at predetermined interval. As to the pressurizing interval at such a case, if synchronizing with pulsations, the effects are more heightened.

Fifth Embodiment

Figure 8:
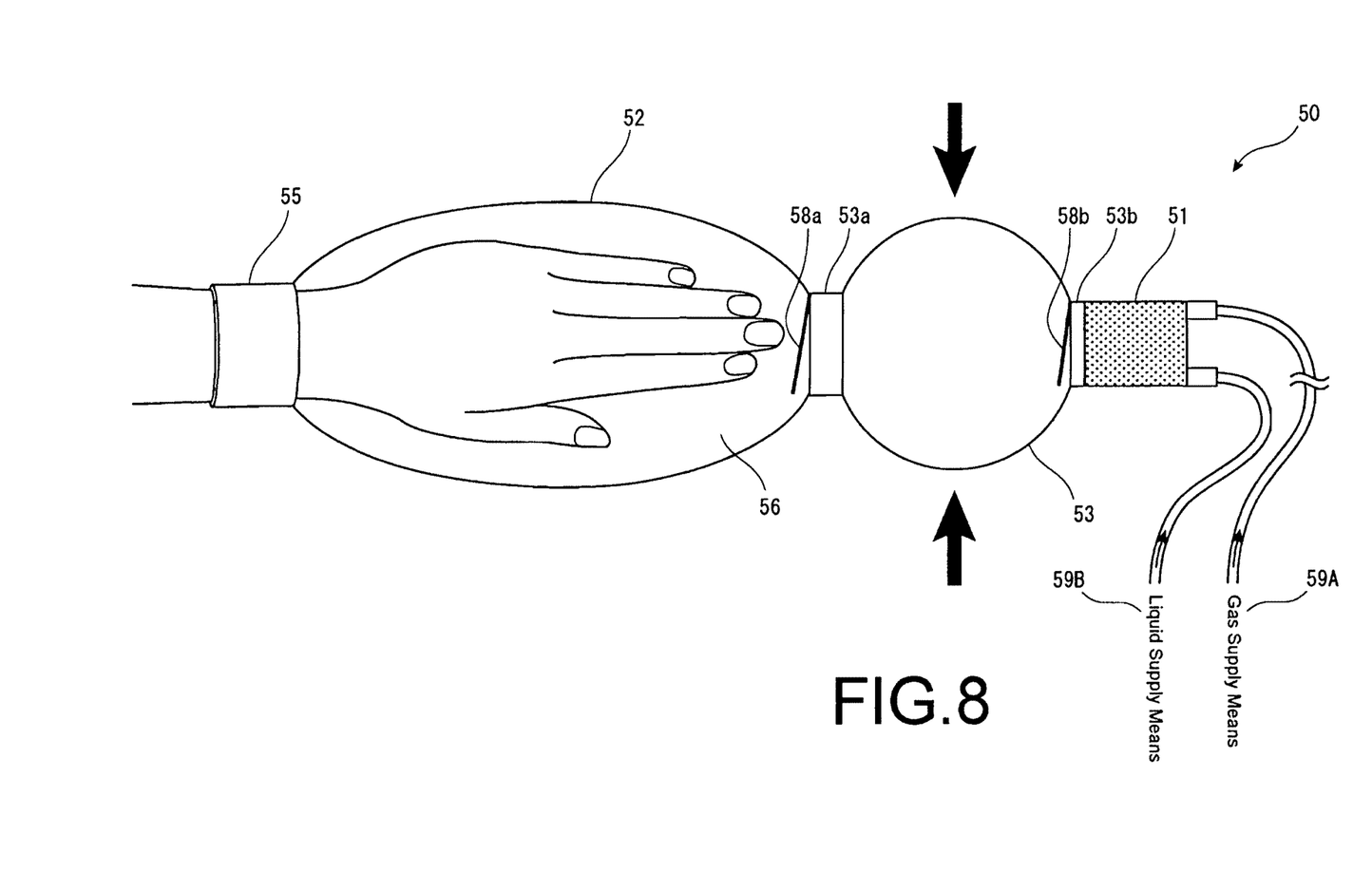
FIG. 8 A generally schematic view of the gas mist pressure bath device depending on a fifth embodiment of the invention.

FIG. 8 is a generally schematic view of the gas mist pressure bath device depending on a fifth embodiment of the invention. The gas mist pressure bath device of this embodiment has the same structure of the first embodiment other than the structure in relation with the shape of the living-body pressure bath cover, and explanation thereof will be omitted in the following.

The gas mist pressure bath device 50 of the present embodiment is, as shown in FIG. 8, composed of the gas mist generating device 51 of supplying the gas mist, the living-body pressure bath cover 52 of the bag shape covering the user's limited part (herein, as the example, the human body's hand) for causing the skin or mucous membrane of this living part to directly contact the gas mist, and an air sending part 53 as the pressurizing means of the living-body cover member connected to the living-body pressure bath cover 52 via a connection part 53a. The bag shaped living-body pressure bath cover 52 of this embodiment has an opening communicating with the air sending part 53, and the opening is connected to the air sending part 53 through the connection part 53a.

The air sending part 53 is formed with the gas mist supply mouth 53b. To this pressurizing ring mouth 53b, the gas mist generating device 51 is directly connected. The gas mist generating device 51 is composed of, for example, a binary nozzle. The binary nozzle mixes liquid and fluid (herein, carbon dioxide, oxygen, or the mixed gas of carbon dioxide and oxygen), changes liquid into fine mists, and atomizes together with air. As shown in FIG. 8, the gas mist generating device 51 of this embodiment is connected to a gas supply means 59A and a liquid supply means 59B. Liquid supplied at this time is preferably about 40 to 70° C.

In regard to liquid to be used for generating the gas mist as mentioned above, other than water, ion water or physiological salt solution, it is preferable to use medical liquids useful to users' diseases, symptoms or other conditions, such as anti-allergic agent, anti-inflammatory agent, anti-analgesic and febrile agent, anti-fungus agent, or anti-influenza virus. This liquid is further possible to generate a synergistic effect with a gas physiological action by coupling with single or plurality of menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic moderating irritation to the mucous membrane; cyclodextrin removing odor; a complex of photocatalysis and apatite having disinfection and anti-phlogistic; hyaluronic acid having excellent water holding capacity and a skin moisture retention effect; coenzyme Q10 activating cells and heightening immunization; a seed oil containing anti-oxidation and much nutrient; or propolith having anti-oxidation, anti-fungus, anti-inflammatory agent, pain-killing, anesthetic, and immunity. Further, high density carbonate spring agent having main components of carbonate and organic acid (as one example of active ingredients, sulfate, carbonate, organic acid or sodium dichloroisocyanurate) may be added.

The connecting part 53a between the living-body pressure bath cover 52 and the air sending part 53 and a gas mist supply mouth 53b are formed with check valves 58a, 58b for avoiding back flow of the gas mist.

For practicing the gas mist pressure bath, the gas mist generating device 51 connected with the gas supply means 59A and the liquid supply means 59B is connected to the gas mist supply mouth 53b of the air sending part 53. Next, the connecting part 53a of the air sending part 53 is connected with the living-body pressure bath cover 52. At this time, air in the air sending part 53 is in advance extracted as much as possible. The bag shaped living-body pressure bath cover 52 is expanded for inserting the user's limited part to be effected with the gas mist pressure bath. Under a condition of extracting air in the living-body pressure bath cover 52 as much as possible, the stopper 55 is attached to make substantially closed in the living-body pressure bath cover 52. Subsequently, gas and liquid are supplied to the gas mist generating device 51 from the gas supply means 59A and the liquid supply means 59B. The gas mist generating device 51 sprays the gas mist into the air sending part 53. By pressurizing the air sensing part 53, the gas mist is moderately sent to the gas mist storage 56 within the living-body pressure bath cover 52, and when the gas mist of the necessary minimum collects in the gas mist storage 56 and the air sending part 53, supplying of gas and liquid from the gas supply means 59A and the liquid supply means 59B is stopped. By pressurizing the air supply part 53 as crashed, carbon dioxide and mist are excluded to the side of the gas mist storage 56, and the inside of living-body pressure bath cover 52 is pressurized moderately (around 1.02 to 2.5 air pressure). Thereby, the gas mist filled within the living-body pressure bath cover 52 is efficiently absorbed into the skin or mucous membrane.

By the way, living-body pressure bath cover 52 and the air sending part 53 may be formed as one body.

The above embodiments are structured to manually press the air sending part 53, but may be carried out mechanically by, for example, the driving device. In addition, since pressurization in the gas mist pressure bath heightens the effects by pressurizing in pulsing at predetermined interval, the effect is heightened, and therefore, the air sending part 53 is sufficient. As to the pressurizing interval at such a case, if synchronizing with pulsations, the effects are more heightened.

Figure 9:
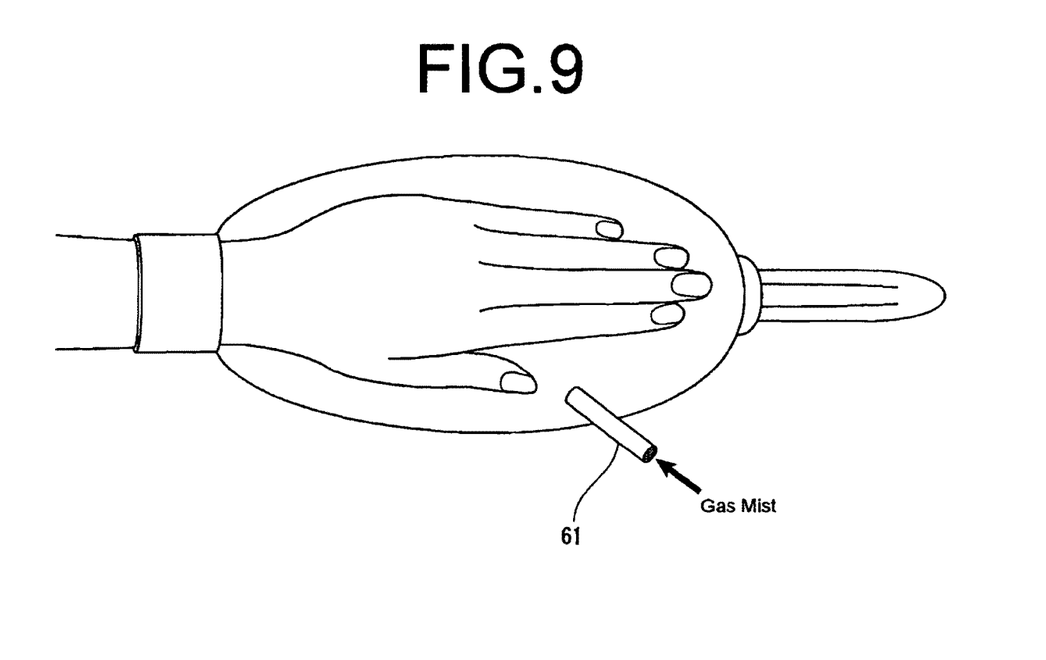
FIG. 9 A typical view showing the gas mist supply mouth of the gas mist pressure bath device depending on the invention.

In the above mentioned first to fourth embodiments, with respect to the structure, the pipe for supplying the gas mist is inserted into the opening of the living-body pressure bath cover and fixed with the stopper for introducing the gas mist into the living-body pressure bath cover. However, the present invention is not limited to such embodiments, and for example, as seen in FIG. 9, the living-body pressure bath cover (gas mist storage) is in advance provided with a gas mist supply mouth 61 to which the pressurizing ring pipe may be connected. Then, the gas mist supply mouth 61 is furnished inside with the check valve.

Omitting illustrations in the above embodiments, the living-body pressure bath cover and the pressurizing means of the living-body cover member may be inserted inside with a gas density measuring instrument (carbon dioxide density measuring instrument and oxygen density measuring instrument) or pressure gauge.

Being constructed as above mentioned, the gas mist pressure bath device of this invention, it is not necessary to fill the gas mist overall the living-body pressure bath cover, and since each adjustment may be possible in view of each part of the inserted living-body, the highly effective gas mist pressure bath can be performed as controlling the gas using amount to minimum.

Further, being very simple structure, any one can easily use without requesting large scaled equipment or selecting operating places. Comparing with the prior art, a production cost can be reduced.

The above explanation has been made to the embodiments of the invention, but the invention is not limited to such embodiments, and so far as not deviating from the subject matter of the invention, various kinds of embodiments are, of course, available.

INDUSTRIAL APPLICABILITY

Thus, the present invention relates the gas mist pressure bath device, in which the gas mist is prepared by pulverizing and dissolving carbon dioxide and oxygen or the mixed gas of carbon dioxide and oxygen, and the gas mist is directly contacted to the skin or mucous membrane of the living-body for improving the blood circulation of the living-body, and has an industrial applicability.

DESCRIPTION OF SYMBOLS 10, 20, 30, 40, 50: Gas mist pressure bath device
11, 21, 31, 41, 51: Gas mist generating device
12, 22, 32, 42, 52: Living-body pressure bath cover 12*a* 32*a*: End
12*b*, 12*b*-1, 12*b*-2: Rib
13: Reducing ring
14, 24, 34, 44: Gas mist supply pipe
14B: Cornice shaped pipe
15, 25, 35, 45, 55: Stopper
16, 26, 36, 46, 56: Gas mist storage
22*a*, 32*b*: Narrowed portion
23, 47: Pressing part
23*a*: Pressing part cover
33: Pressing ring
42*a*: Shielding film
43: Syringe
47*a*, 53*a*: Connecting part
53: Air sending part
53*b*: Gas mist supply mouth
58*a*, 58*b*: Check valve
59A: Gas supply means
59B: Liquid supply means, and
61: Gas mist supply mouth

The invention claimed is:

1. A gas mist pressure bath device for contacting oxygen, carbon dioxide or a mixed gas of oxygen and carbon dioxide with a skin or a mucous membrane of a living-body, comprising:
a gas mist generating device for generating gas mist by contacting the oxygen, the carbon dioxide or the mixed gas of oxygen and carbon dioxide, with fine liquid drops and for supplying the gas mist;

a living-body cover member having a bag shape for covering the skin or the mucous membrane of the living-body and sealing the gas mist from the gas mist generating device therein, the living-body cover member including an opening portion and a plurality of ribs integrally formed at an end of the living-body cover member, the end being opposite to the opening portion and the living-body being inserted into the living-body cover member from the opening portion; and a pressurizing ring for pressurizing the gas mist within the living-body cover member, the pressurizing ring having a hole portion and being made of an elastic member, wherein, when a gas mist pressure bathing is performed, after the gas mist is supplied from the gas mist generating device to the living-body cover member, the end of the living-body cover member passes into the hole portion of the pressurizing ring and the pressurizing ring slides along the plurality of ribs from the end toward the opening portion of the living-body cover member such that a capacity of the living-body cover member is reduced to pressurize an inside of the living-body cover member, and the gas mist sealed within the living-body cover member contacts with the skin or the mucous membrane of the living body at a predetermined pressure;

wherein the gas mist generating device has a gas mist supply pipe for supplying the gas mist into the living-body cover member and the gas mist supply pipe is inserted through the opening portion together with the living-body.

2. A gas mist pressure bath device for contacting oxygen, carbon dioxide or a mixed gas of oxygen and carbon dioxide with a skin or a mucous membrane of a living-body, comprising:
a gas mist generating device for generating gas mist including by contacting the oxygen, the carbon dioxide or the mixed gas of oxygen and carbon dioxide, with fine liquid drops and for supplying the gas mist;

a living-body cover member having a bag shape for covering the skin or the mucous membrane of the living body and for sealing the gas mist from the gas mist generating device therein, the living-body cover member including a insertion part and a pressurizing part connecting to the insertion part; and a pressurizing member including a shielding film and a syringe, the shielding film being made of an elastic member and being positioned in the living-body cover member to partition an inside of the living-body cover member into the insertion part and the pressurizing part, and the syringe being positioned outside of the living-body cover member and being connected to the pressurizing part, wherein the syringe sends air into the pressurizing part, thereby the shielding film expands in a direction from the pressurizing part toward the insertion part so that the gas mist within the insertion part is pressurized;

wherein the gas mist generating device has a gas mist supply pipe for supplying the gas mist into the living-body cover member and the insertion part has an opening portion at one end portion opposite to the pressurizing part for inserting the living-body into the living-body cover member; and the gas mist supply pipe is inserted through the opening portion together with the living-body.

3. A gas mist pressure bath device as set forth in claim 1, wherein the living-body cover member has, at the opening portion thereof, a fastener fabricated with at least one of a rubber, a string and a face fastener to avoid the gas mist leaking into atmosphere.

4. A gas mist pressure bath device as set forth in claim 1, wherein the living-body cover member further includes at least one adhesive having viscosity on a face thereof contacting the skin or the mucous member.

5. A gas mist pressure bath device as set forth in claim 1, wherein a particle size of the gas mist supplied from the gas mist generating device to the living-body cover member is not more than 10 micrometers.

6. A gas mist pressure bath device as set forth in claim 1, wherein interval pressurization is carried out by the pressurizing ring.

7. A gas mist pressure bath device as set forth in claim 1, wherein the living-body cover member is formed with at least one material selected from the group consisting of a natural rubber, silicone rubber, polyethylene, polypropylene, polyvinylidene chloride, polystyrene, polyvinyl acetate, polyvinyl chloride, polyamide resin, polytetrafluoroethylene, woven fabric, and nonwoven fabric.

8. A gas mist pressure bath device as set forth in claim 1, wherein the gas mist generating device has a gas mist supply pipe for supplying the gas mist into the living-body cover member, and at least one part of the gas mist supply pipe is pleated.

9. A gas mist pressure bath device as set forth in claim 2, wherein the living-body cover member further includes a connecting part formed at a side opposite to the insertion part, and the syringe connects the living-body cover member through the connecting part to send the air into only the pressurizing part.

10. A gas mist pressure bath device as set forth in claim 2, wherein the shielding film is a flat film, the insertion part is defined by the living-body cover member and on side of the shielding film, and the pressurizing part is defined by the living-body cover member and another side of the shielding film.

* * * * *